United States Patent
Park et al.

(10) Patent No.: US 11,307,185 B2
(45) Date of Patent: Apr. 19, 2022

(54) AIR-QUALITY DETECTION APPARATUS

(71) Applicant: LG ELECTRONICS INC., Seoul (KR)

(72) Inventors: Chiwan Park, Seoul (KR); Kijung Sung, Seoul (KR); Hyunho Oh, Seoul (KR); Taedong Shin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 303 days.

(21) Appl. No.: 16/705,762

(22) Filed: Dec. 6, 2019

(65) Prior Publication Data
US 2020/0182843 A1 Jun. 11, 2020

(30) Foreign Application Priority Data
Dec. 7, 2018 (KR) .......................... 10-2018-0157579

(51) Int. Cl.
*G01N 33/00* (2006.01)
*H05K 1/14* (2006.01)
*H05K 1/18* (2006.01)

(52) U.S. Cl.
CPC ......... *G01N 33/0031* (2013.01); *H05K 1/144* (2013.01); *H05K 1/18* (2013.01); *H05K 2201/10151* (2013.01)

(58) Field of Classification Search
CPC ...... G01N 33/0031; H05K 1/144; H05K 1/18; H05K 2201/10151
USPC ....................................................... 73/28.01
See application file for complete search history.

(56) References Cited

U.S. PATENT DOCUMENTS

| | | | |
|---|---|---|---|
| 6,782,351 B2 | 8/2004 | Reichel et al. | |
| 9,993,166 B1 * | 6/2018 | Johnson | A61B 5/0022 |
| 11,030,875 B2 | 6/2021 | Glynn | |
| 11,184,739 B1 | 11/2021 | Wellig | |
| 2009/0308941 A1 | 12/2009 | Patch | |

(Continued)

FOREIGN PATENT DOCUMENTS

| | | |
|---|---|---|
| CH | 710015 | 2/2016 |
| CN | 204501797 | 7/2015 |

(Continued)

OTHER PUBLICATIONS

Korean Office Action dated Feb. 4, 2020.
(Continued)

*Primary Examiner* — Nathaniel T Woodward
(74) *Attorney, Agent, or Firm* — Ked & Associates LLP

(57) ABSTRACT

Disclosed is an air-quality detection apparatus including a casing body including a bottom and a side wall, a first printed circuit board (PCB) disposed horizontally above the bottom, a second PCB disposed horizontally in a first region above the first PCB, a $CO_2$ sensor mounted on the second PCB, a volatile organic compound (VOC) sensor mounted in a second region on the first PCB that is closer to the side wall than the first region, a third PCB, which is disposed horizontally at a position spaced further upwards apart from the bottom than the first PCB and at least a portion of which is disposed in a third region that does not overlap the first PCB when the bottom is viewed from above, a fourth PCB disposed horizontally above the second PCB and the third PCB, and a dust sensor mounted on the fourth PCB.

12 Claims, 15 Drawing Sheets

(56) References Cited

U.S. PATENT DOCUMENTS

| | | |
|---|---|---|
| 2017/0241964 A1 | 8/2017 | Vereecken |
| 2017/0257967 A1 | 9/2017 | Obrist |
| 2019/0154286 A1 | 5/2019 | Pham |
| 2020/0049365 A1 | 2/2020 | Thoni |
| 2020/0261009 A1 | 8/2020 | Everman |
| 2021/0239335 A1 | 8/2021 | Morgan |
| 2021/0393834 A1 | 12/2021 | Wellig |
| 2021/0398230 A1 | 12/2021 | Gupta |
| 2022/0001999 A1 | 1/2022 | Pearce |

FOREIGN PATENT DOCUMENTS

| | | |
|---|---|---|
| CN | 105823515 | 8/2016 |
| CN | 106813315 | 6/2017 |
| CN | 108896105 | 11/2018 |
| DE | 20-2017-106413 | 10/2017 |
| EP | 3 070 800 | 9/2016 |
| KR | 10-2003-0010431 | 2/2003 |
| KR | 10-2008-0048929 | 6/2008 |
| KR | 10-2009-0052167 | 5/2009 |
| KR | 10-2009-0067731 | 6/2009 |
| KR | 10-2017-0076254 | 7/2017 |
| KR | 10-2018-006228 | 6/2018 |
| KR | 10-2018-0062628 | 6/2018 |
| KR | 10-1912624 | 10/2018 |
| WO | WO 2016/030082 | 3/2016 |
| WO | WO 2018/215980 | 11/2018 |

OTHER PUBLICATIONS

European Search Report dated May 13, 2020.
Indoor air quality module Ultra fine dust sensor, CO2 sensor, VOC sensor, temperature and humidity sensor, integrated indoor air quality management module; Cubic Dust Sensor Korean Agency FIS Korea Agency; pp. 1-2; blog.daum.net/kurayamida/17.
European Search Report dated May 20, 2020 issued in Application No. 19214169.5.
Korean Notice of Allowance dated Sep. 4, 2020 issued in Application No. 10-2018-0157579.
U.S. Appl. No. 16/705,695, filed Dec. 6, 2019.
U.S. Notice of Allowance issued in U.S. Appl. No. 16/705,695 dated Feb. 25, 2022.
U.S. Office Action issued in U.S. Appl. No. 16/705,695 dated Feb. 25, 2022.

* cited by examiner

AIR-QUALITY DETECTION APPARATUS

CROSS-REFERENCE TO RELATED APPLICATION

This application claims priority under 35 U.S.C. § 119 to Korean Application No. 10-2018-0157579 filed on Dec. 7, 2018, whose entire disclosure is hereby incorporated by reference.

BACKGROUND

1. Field

The present disclosure relates to an apparatus for detecting the quality of air.

2. Background

Sensors for detecting the quality of indoor/outdoor air are known. Recently, as it has become generally known that fine dust (PM 10) or ultra-fine dust (PM 2.5) is harmful to the human body, sensors for detecting the quality of indoor/outdoor air have greatly attracted the attention of the general public.

Korean Patent No. 10-1912624 (hereinafter, referred to as the 'conventional art 1') discloses an outdoor-air-quality detection apparatus that is networked with a user's terminal. The air-quality detection apparatus disclosed in the conventional art 1 is configured to transmit the quality of air detected by a sensor to a network through a communication interface so that a user confirms the quality of air using the user's terminal.

The sensor includes a fine dust sensor, a temperature/humidity sensor, a volatile organic compound detection sensor, and the like, and is configured to detect the overall quality of air.

Although the conventional art 1 suggests that the sensor and the communication interface are mounted on a substrate accommodated in a main body, the concrete structure for mounting these components on the substrate is not described or disclosed.

Since the air-quality detection apparatus of the conventional art 1 is secured to a wall using a fixing frame 40, it is not portable. However, in recent years, since interest in the quality of indoor air in, for example, offices, homes, and the like, as well as the quality of outdoor air is high, a small-sized compact air-quality detection apparatus is required so that a user may easily carry the air-quality detection apparatus and use the same at a desired place.

In particular, when an air-quality detection apparatus is configured to detect the overall quality of air using various types of sensors, it is important not only to compactly arrange the sensors to minimize the volume of the apparatus but also to optimize the arrangement of the sensors so that each sensor does not affect the accuracy of detection by other sensors.

The above reference is incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements wherein.

DETAILED DESCRIPTION

Figure 1:
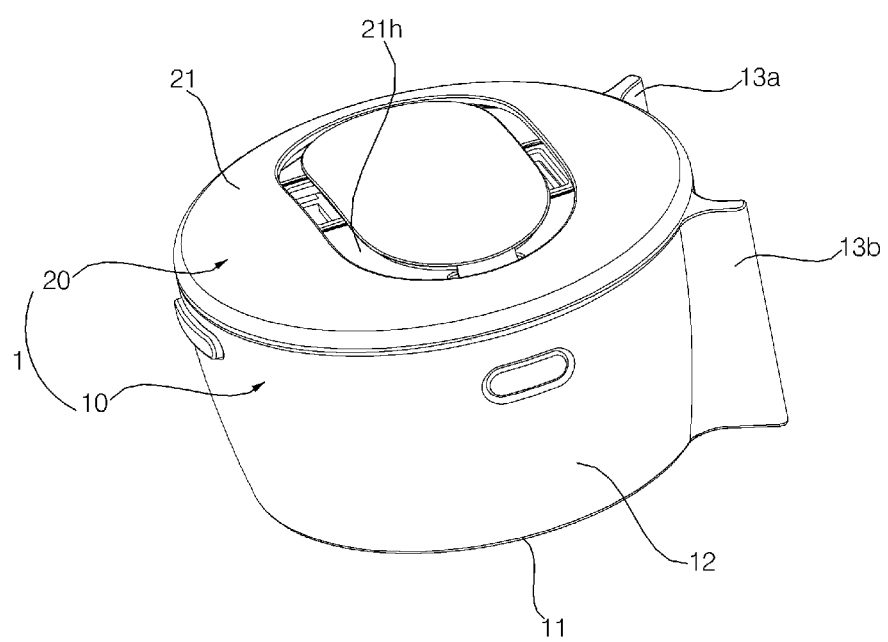
FIG. 1 is a perspective view of an air-quality detection apparatus according to an embodiment of the present disclosure.

Advantages and features of the present disclosure and methods for achieving them will be made clear from the embodiments described below in detail with reference to the accompanying drawings. The present disclosure may, however, be embodied in many different forms, and should not be construed as being limited to the embodiments set forth herein. Rather, these embodiments are provided so that this disclosure will be thorough and complete, and will fully convey the scope of the present disclosure to those skilled in the art. The present disclosure is merely defined by the scope of the claims. Like reference numerals refer to like elements throughout the specification.

Figure 2:
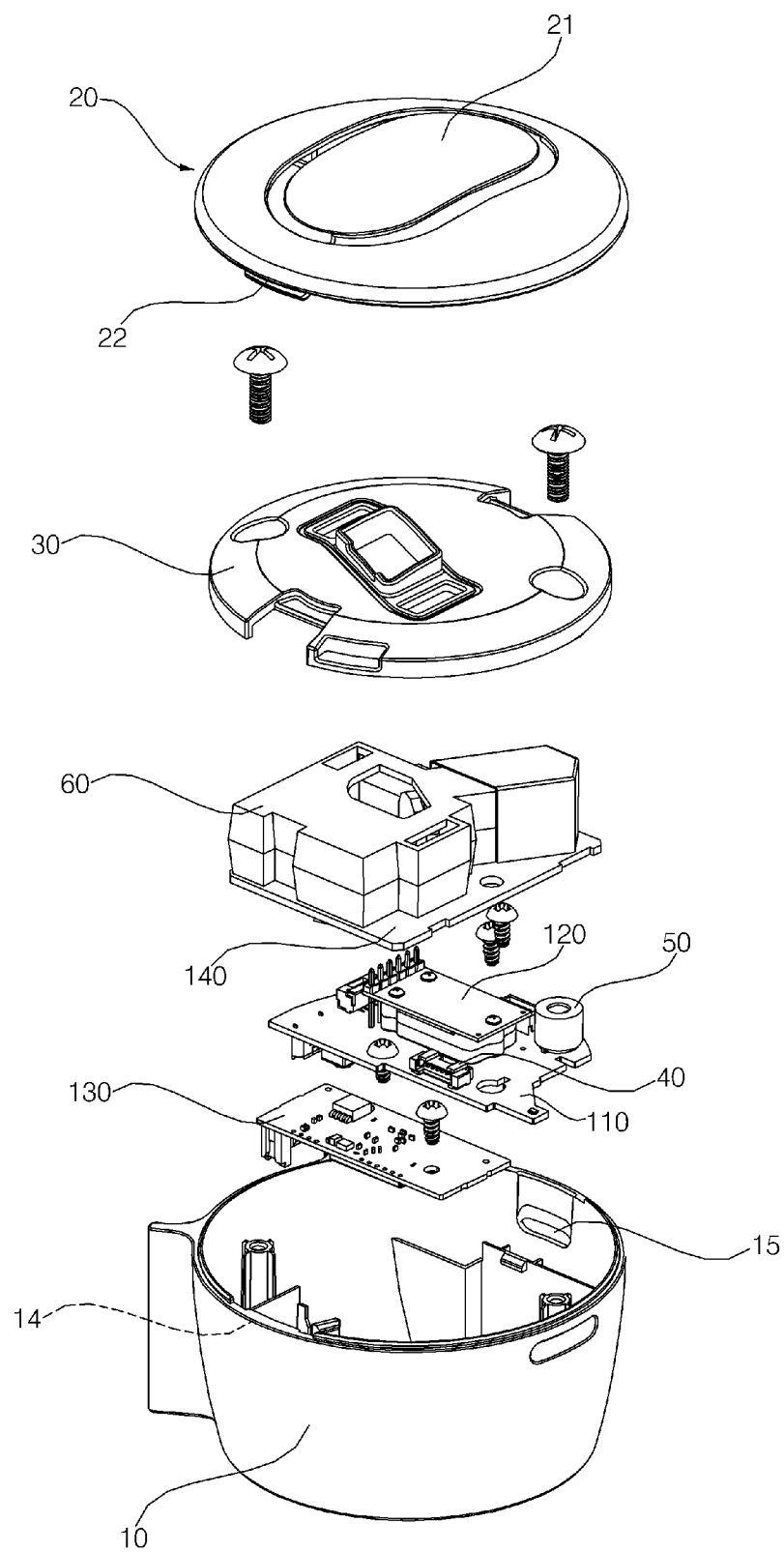
FIG. 2 is an exploded perspective view of the air-quality detection apparatus shown in FIG. 1.

FIG. 1 is a perspective view of an air-quality detection apparatus according to an embodiment of the present disclosure. FIG. 2 is an exploded perspective view of the air-quality detection apparatus shown in FIG. 1. Referring to FIGS. 1 and 2, an air-quality detection apparatus according to an embodiment of the present disclosure includes a casing 1 forming the external appearance of the air-quality detection apparatus, two or more printed circuit boards (PCBs) 110, 120, 130 and 140 disposed in the casing 1, and two or more sensors mounted on the PCBs 110, 120, 130 and 140.

The casing 1 may include a casing body 10, having an open top surface and defining a predetermined accommodation space therein, and an exterior panel 20 covering the open top surface of the casing body 10. The casing body 10 may include a bottom 11 and a side wall 12. The bottom 11 may be formed in a substantially circular and flat shape, and the side wall 12 may be formed in a cylindrical shape extending upwards from the circumference of the bottom 11. The side wall 12 may have a truncated cone shape in which the inner and outer diameters of the cross-section thereof gradually increase toward the upper side thereof (or from the bottom 11 of the casing body 10 to the top surface of the casing body 10).

The casing body 10 may include a pair of stands 13a and 13b protruding from the outer surface of the side wall 12. The pair of stands 13a and 13b may be spaced apart from each other in a circumferential direction, and may protrude from the side wall 12 in a radial direction. The air-quality detection apparatus may stand upright due to the pair of stands 13a and 13b such that the exterior panel 20 is oriented forwards.

The exterior panel 20 may include a lid 21 having a vent hole 21h formed therein, and may further include a hinge lock 22 and a locking hook 23, which protrude from the rear surface of the lid 21. The hinge lock 22 and the locking hook 23 may be disposed at opposite sides of the lid 21 so as to be symmetrical to each other with respect to the center of the lid 21. The vent hole 21h may be formed along a substantially annular-shaped path. However, the vent hole 21h may not be formed in some regions of the path, such that an inner portion of the lid 21, which is surrounded by the path, is connected to an outer portion of the lid 21.

The casing body 10 may have a latching recess 14 formed in the circumference of the open upper end thereof such that the hinge lock 22 is caught therein. In addition, the casing body 10 may have a locking recess 15 formed in the inner surface of the side wall 12 such that the locking hook 23 is caught therein. In order to assemble the exterior panel 20 to the casing body 10, the hinge lock 22 is first fitted into the latching recess 14 by tilting the exterior panel 20 with respect to the casing body 10, and then the locking hook 23 is fitted into the locking recess 15 by rotating the exterior panel 20 about the latching recess 14 such that the locking hook 23 is moved downwards.

A cover 30 covering the casing body 10 may be further provided. The cover 30 is disposed between the casing body 10 and the exterior panel 20 to cover the open top surface of the casing body 10. The cover 30 may have at least one vent hole 31, 32 and 33 formed therein to allow external air to enter the casing body 10. The vent hole 31, 32 and 33 may include a first vent hole 31 formed in the center of the cover 30, and second and third vent holes 32 and 33 formed in regions of the cover 30 on opposite sides of the first vent hole 31.

The cover 30 may have a hinge lock passage 34 and a hook passage 35 formed in regions thereof that respectively correspond to the position of the hinge lock 22 and the position of the locking hook 23, which are formed at the exterior panel 20.

Figure 3:
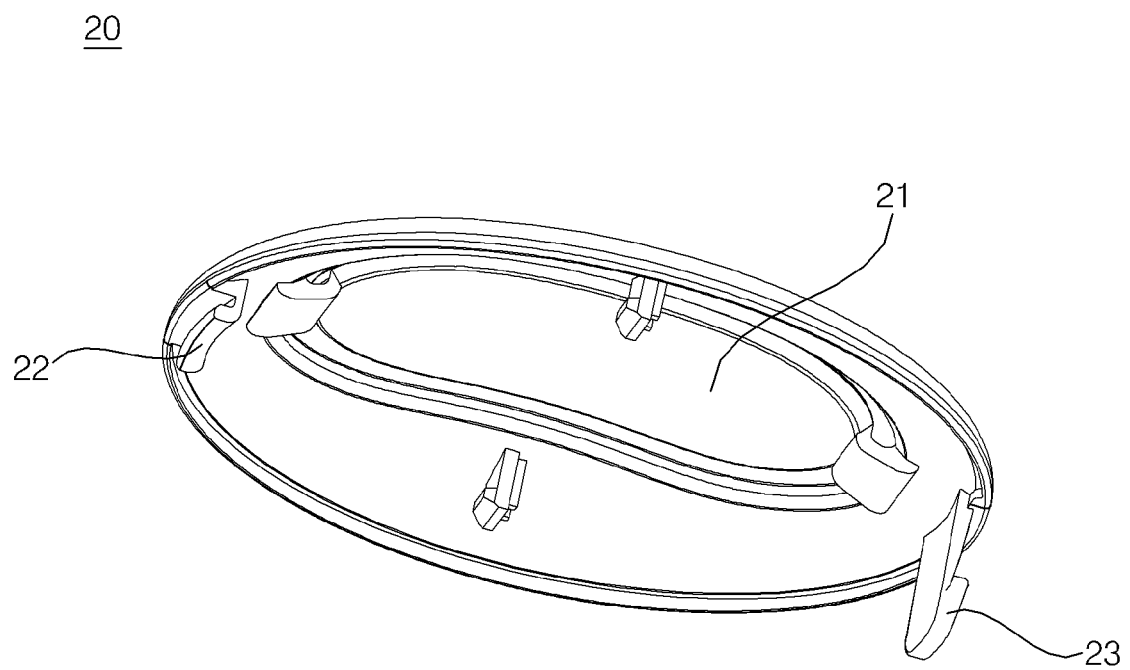
FIG. 3 is a perspective view of the exterior panel shown in FIG. 1.
Figure 4:
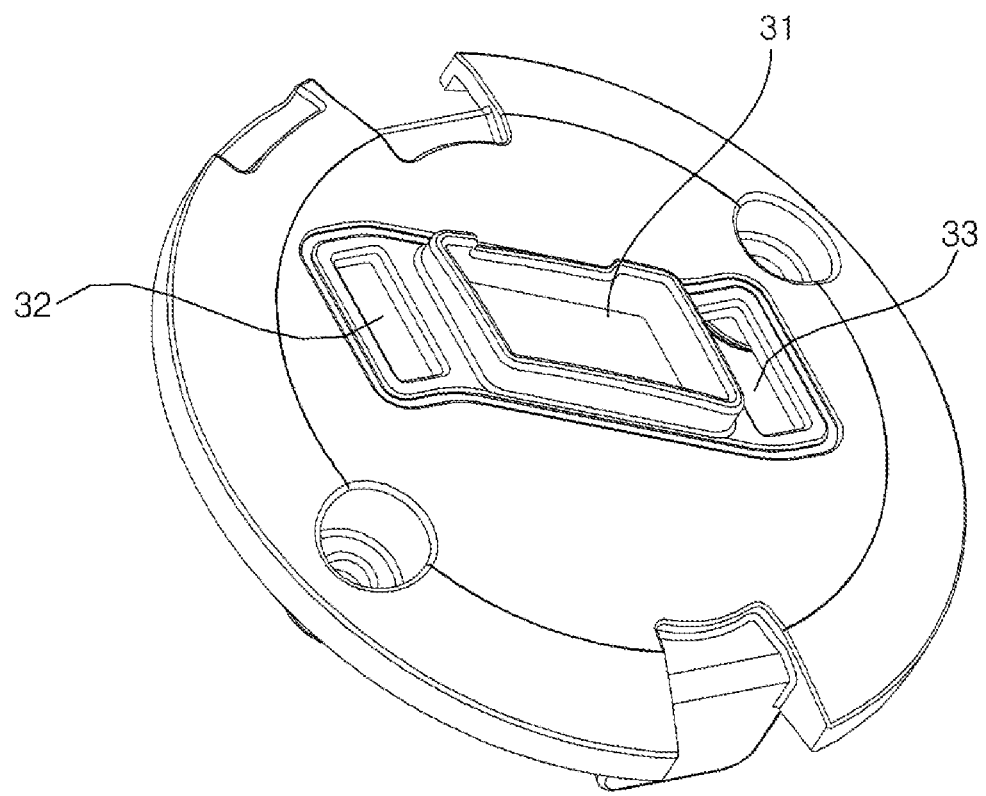
FIG. 4 is a perspective view of the cover shown in FIG. 2.
Figure 5:
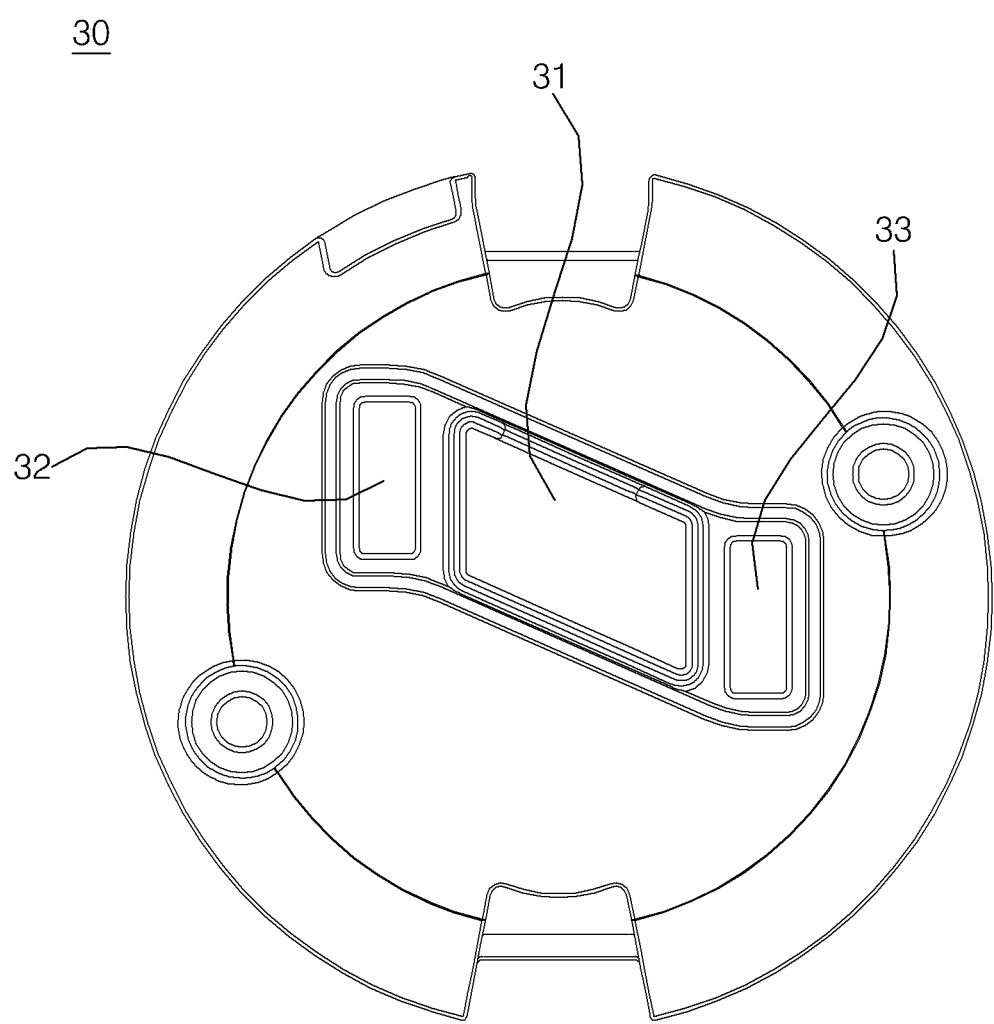
FIG. 5 is a plan view of the cover shown in FIG. 4.
Figure 6:
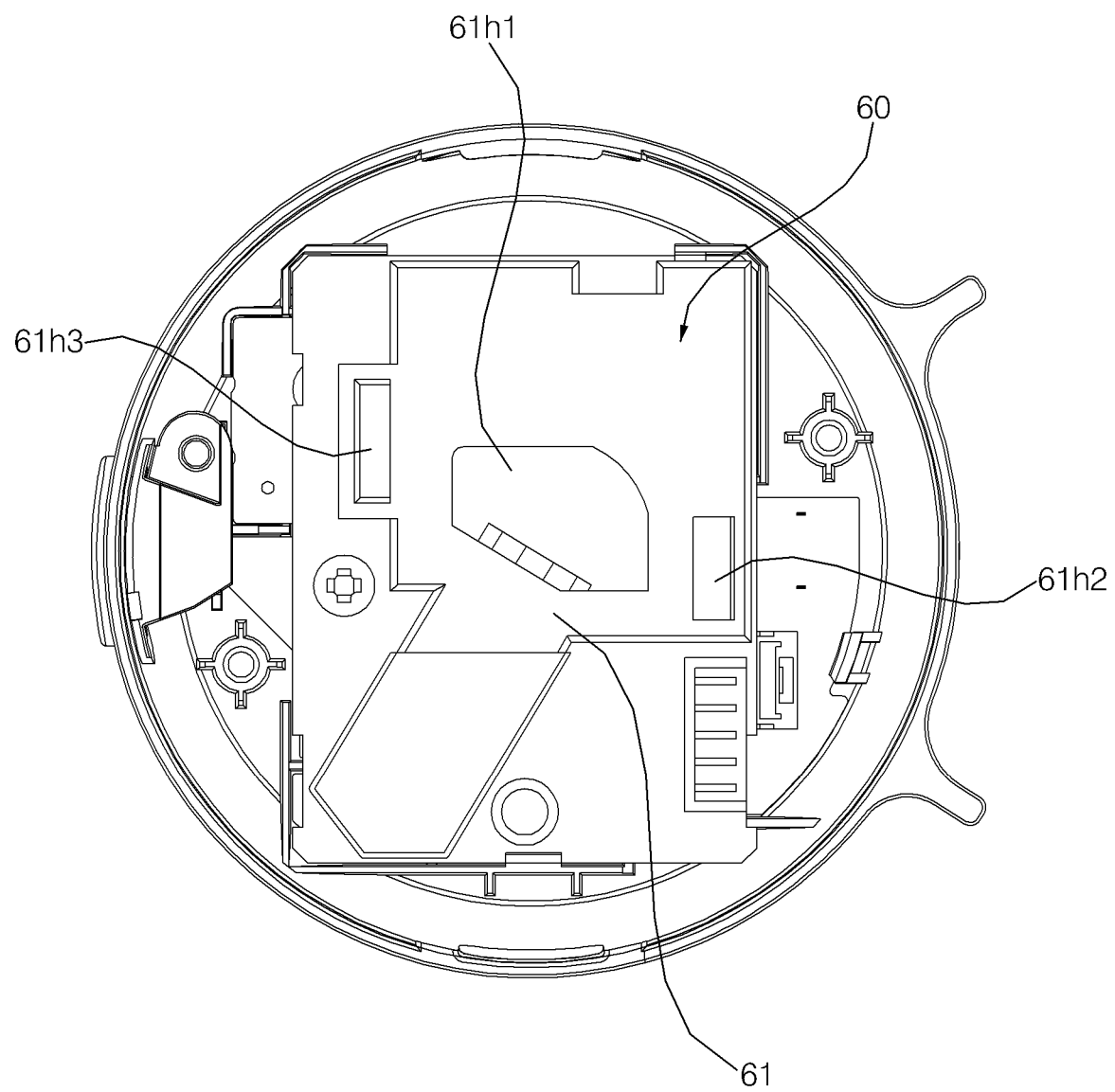
FIG. 6 is a partially exploded view of the air-quality detection apparatus shown in FIG. 1.
Figure 7:
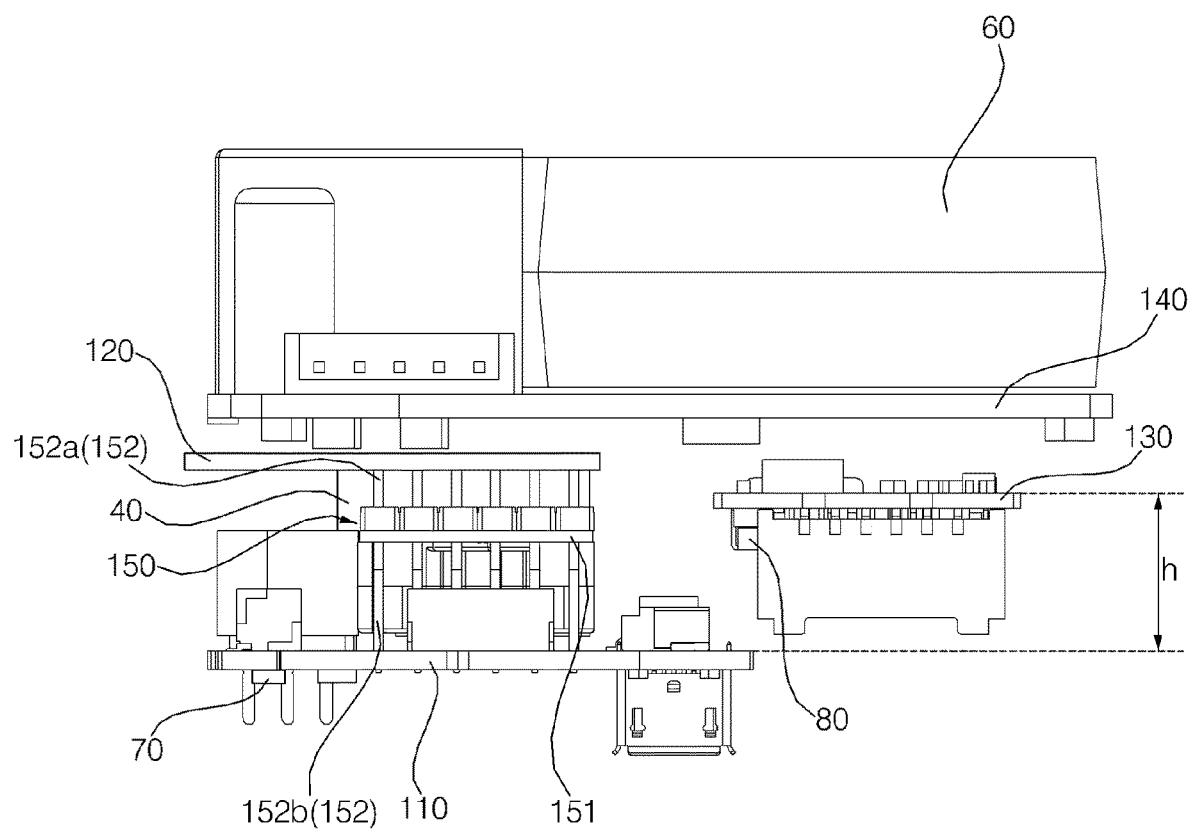
FIG. 7 is a side view of FIG. 6, with a casing body removed.
Figure 8:
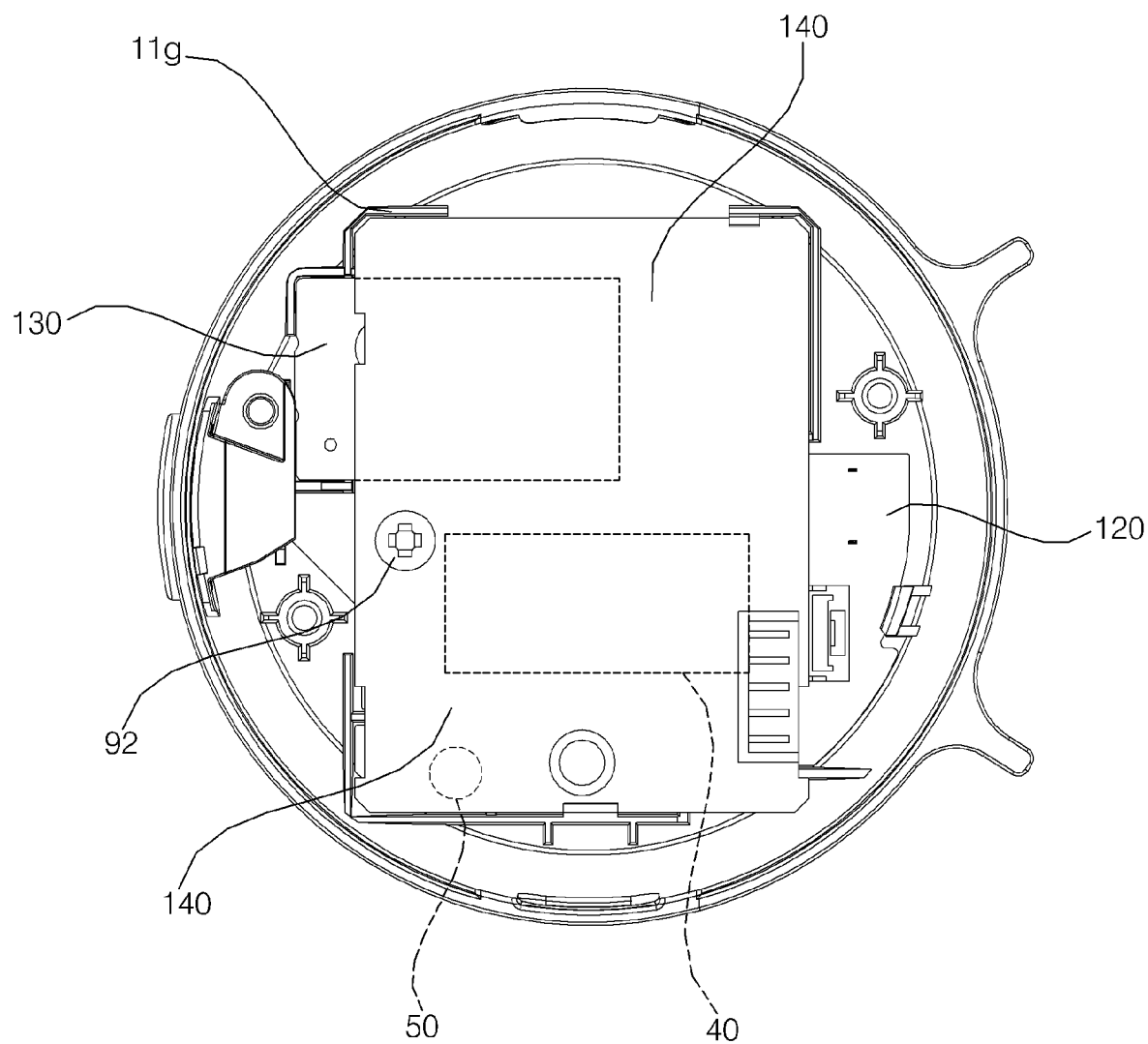
FIG. 8 is a view of the assembly shown in FIG. 6, with a dust sensor removed.
Figure 9:
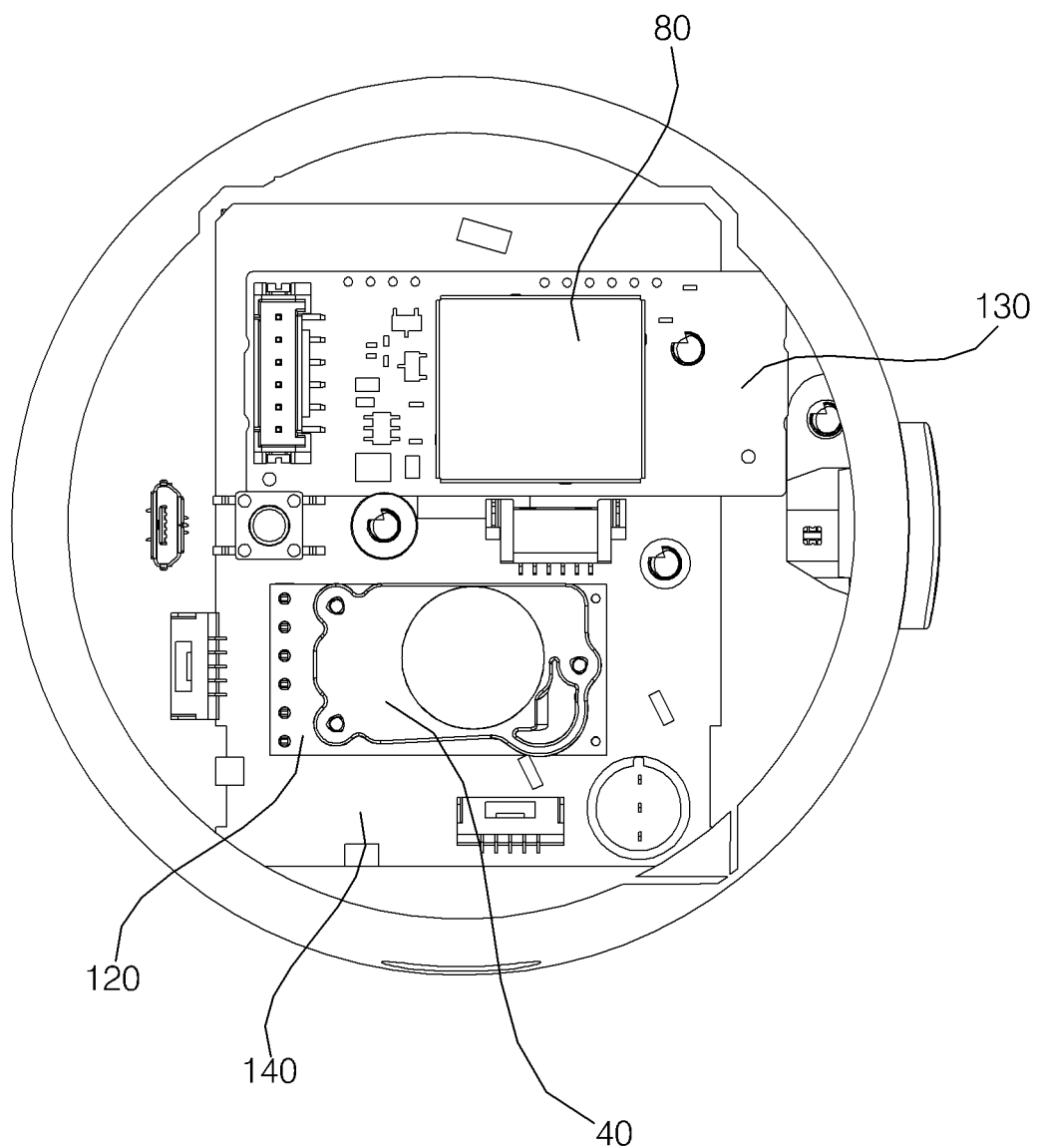
FIG. 9 is a bottom view of a fourth printed circuit board (PCB)
Figure 10:
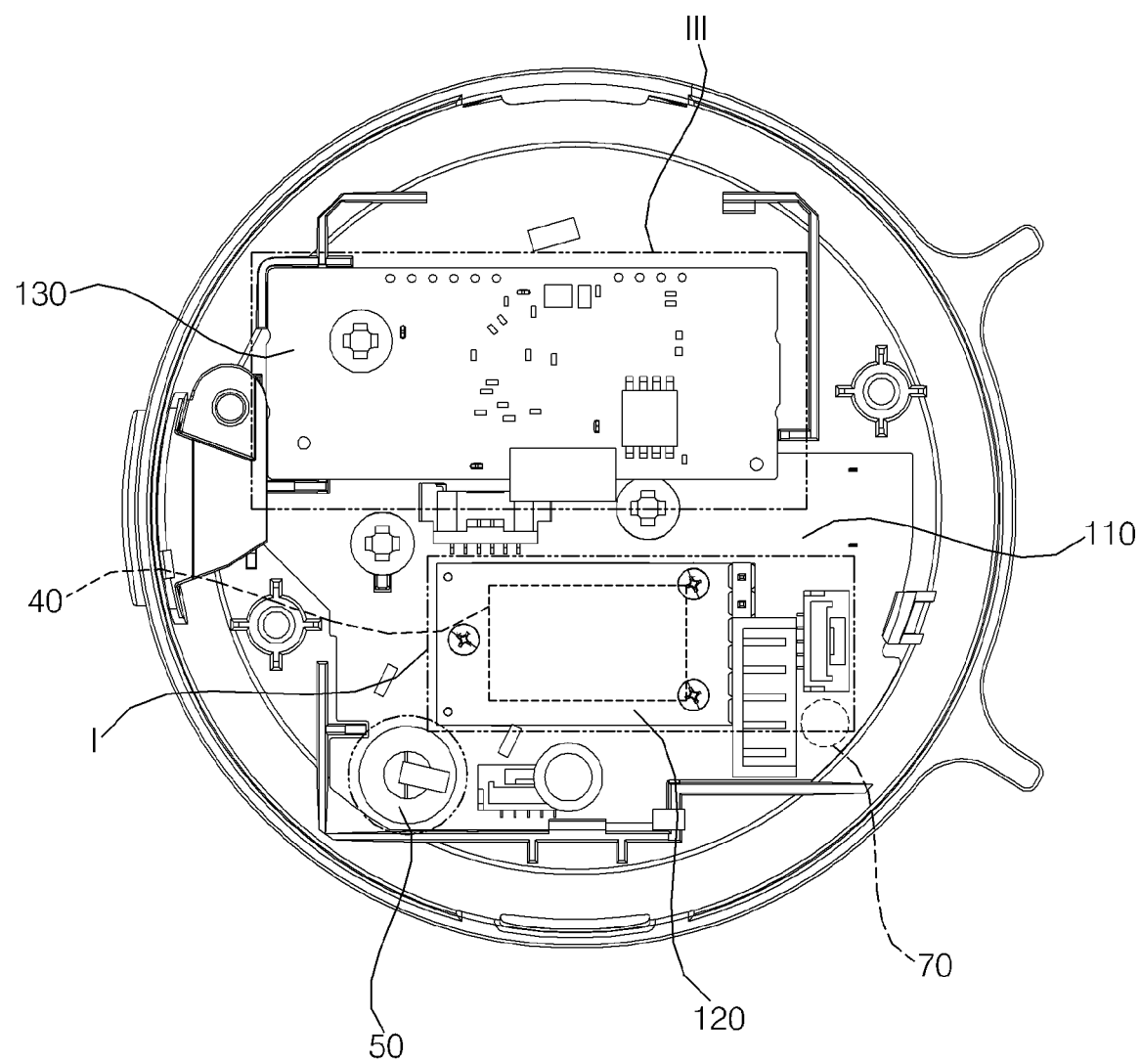
FIG. 10 is a view of the assembly shown in FIG. 8, with the fourth PCB removed.
Figure 11:
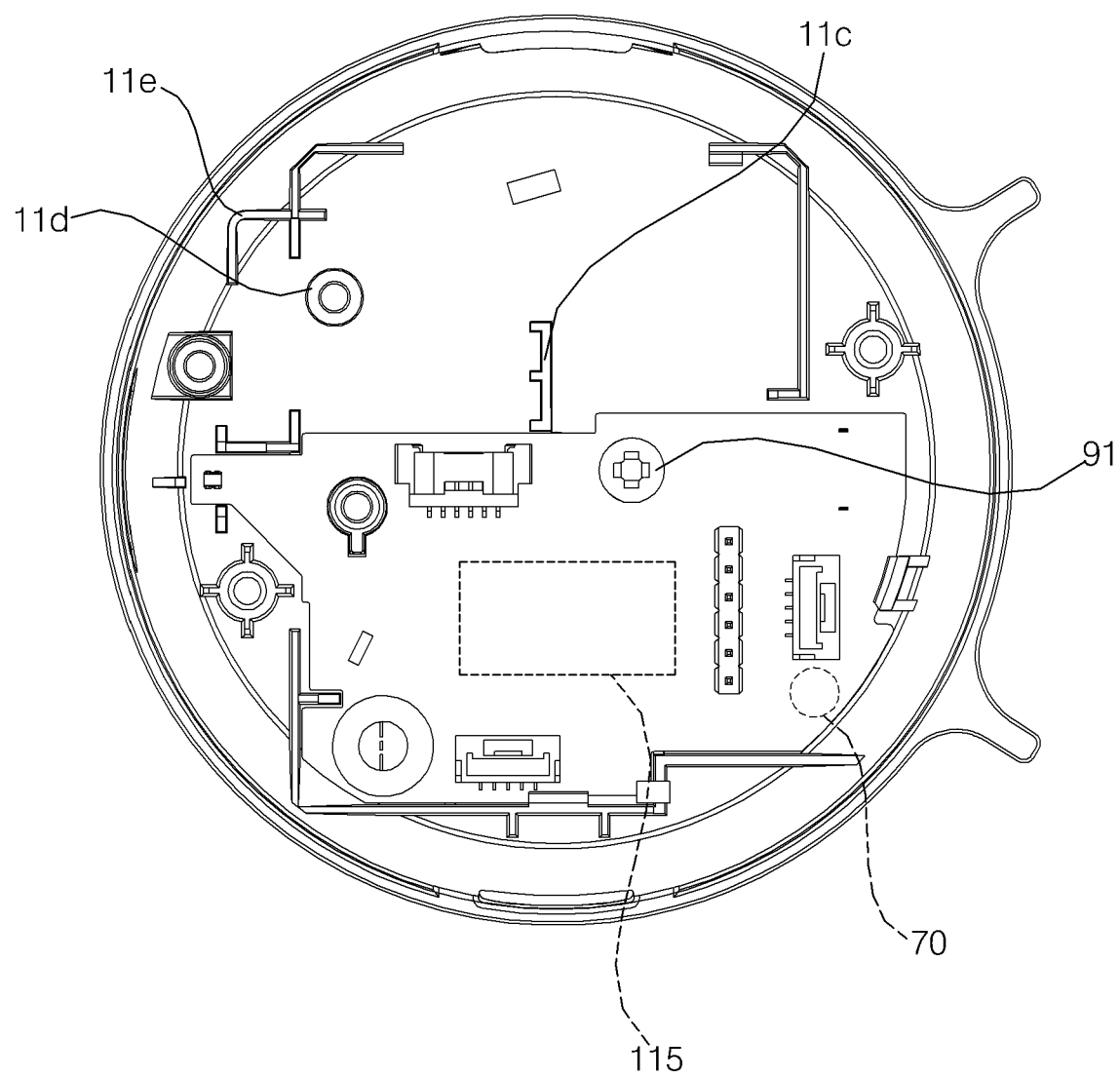
FIG. 11 is a view of the assembly shown in FIG. 10, with a second PCB and a third PCB removed.
Figure 12:
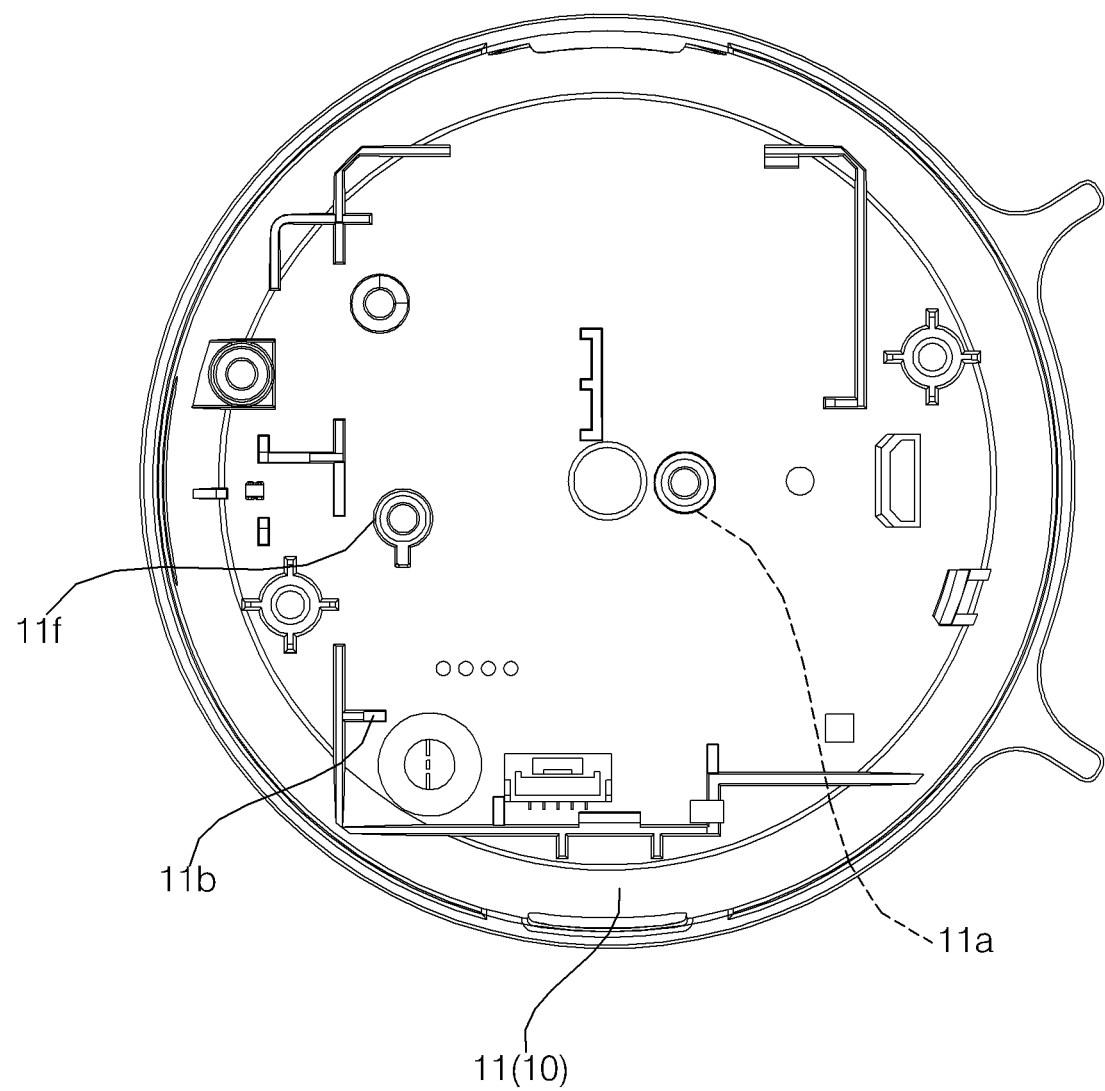
FIGS. 12 and 13 are views of the casing body.
Figure 13:
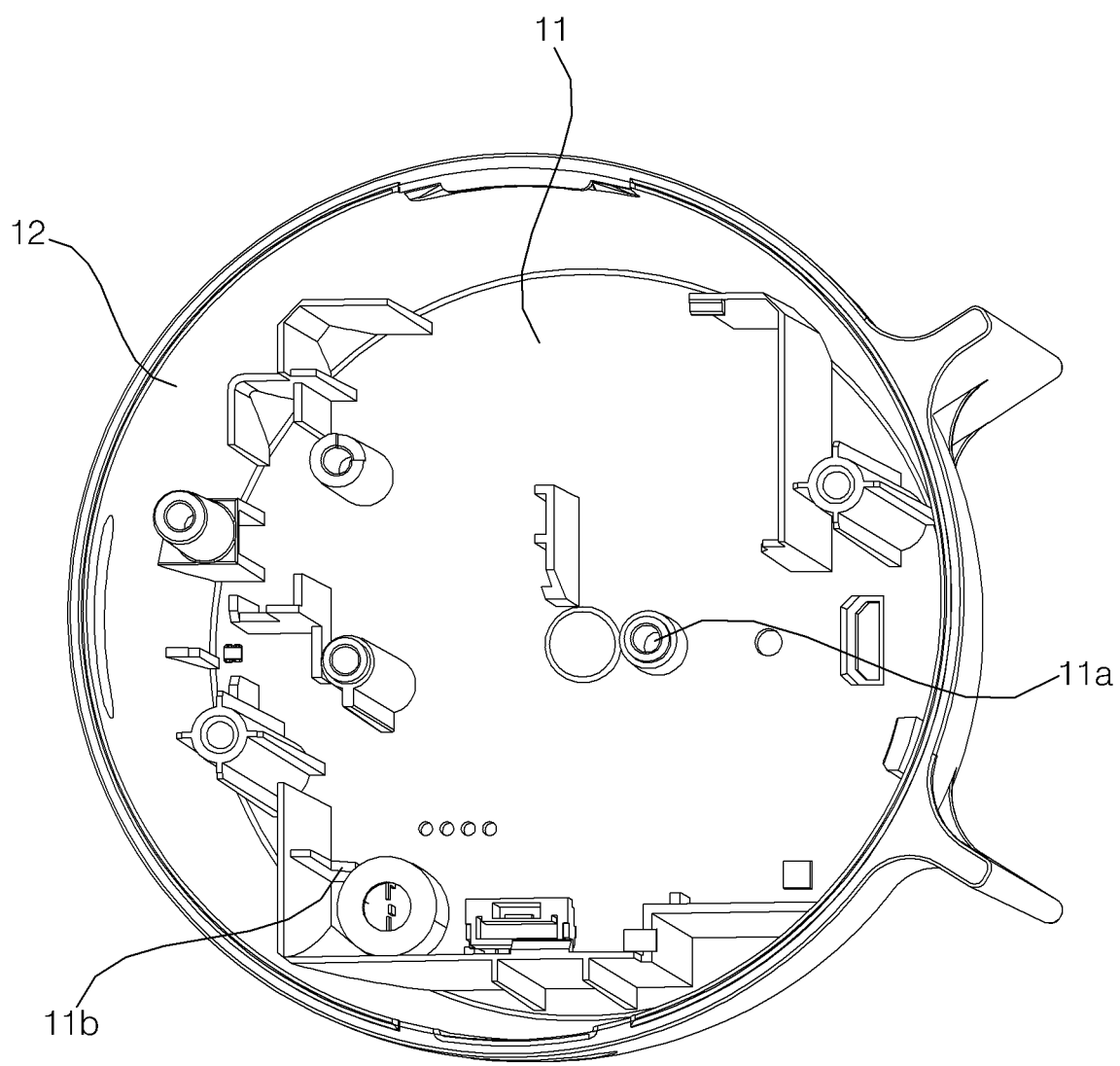
Figure 14:
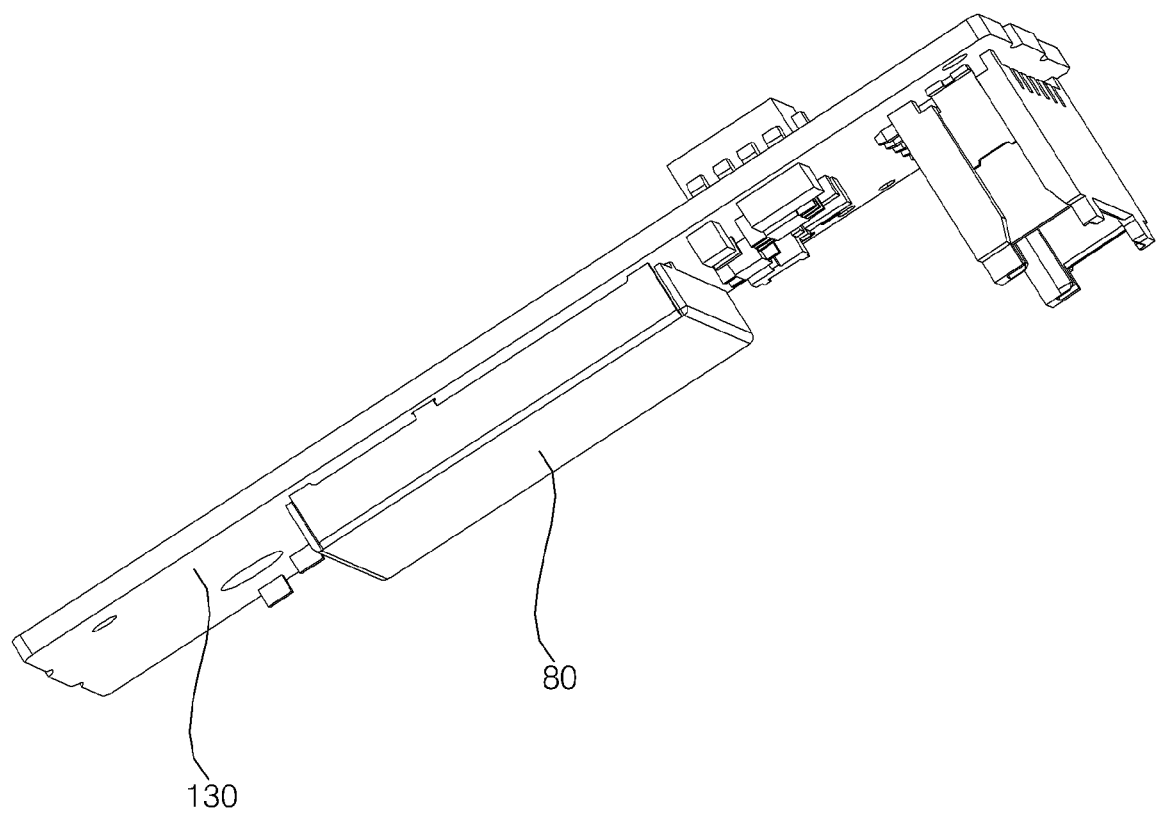
FIG. 14 is a view of the third PCB, on which a wireless communication interface is mounted.
Figure 15:
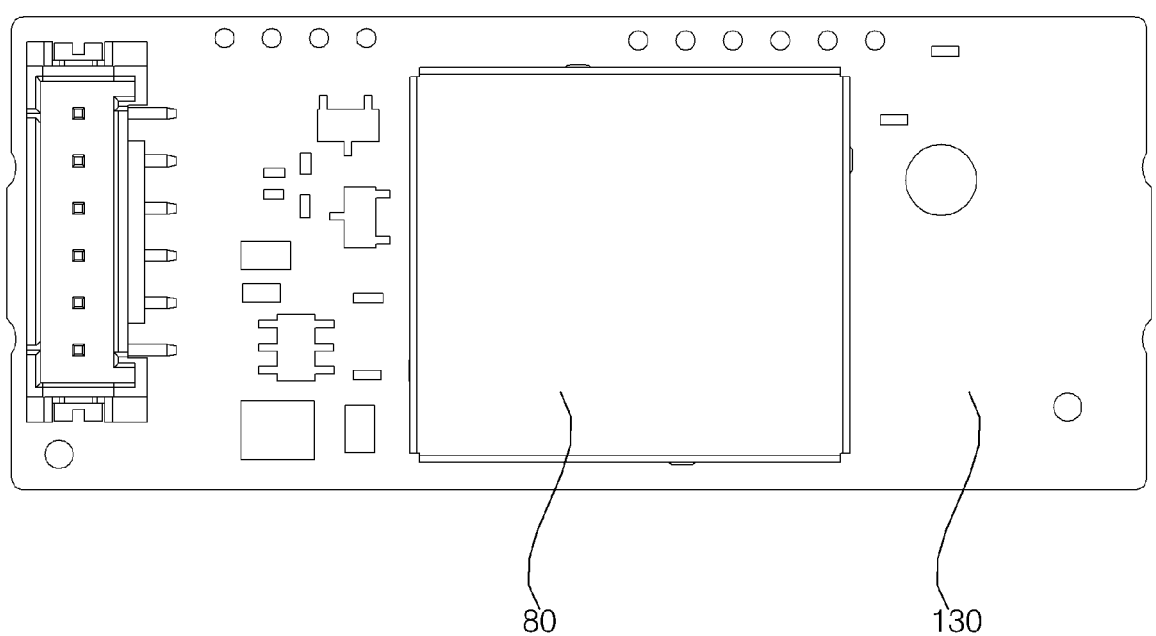
FIG. 15 is a bottom view of FIG. 14.

FIG. 3 is a perspective view of the exterior panel shown in FIG. 1. FIG. 4 is a perspective view of the cover shown in FIG. 3. FIG. 5 is a plan view of the cover shown in FIG. 4. FIG. 6 is a partially exploded view of the air-quality detection apparatus shown in FIG. 1. FIG. 7 is a side view of FIG. 6, with the casing body removed. FIG. 8 is a view of the assembly shown in FIG. 6, with a dust sensor removed. FIG. 9 is a bottom view of a fourth PCB. FIG. 10 is a view of the assembly shown in FIG. 8, with the fourth PCB removed. FIG. 11 is a view of the assembly shown in FIG. 10, with a second PCB and a third PCB removed. FIGS. 12 and 13 are views of the casing body. FIG. 14 is a view of the third PCB, on which a wireless communication interface is mounted. FIG. 15 is a bottom view of FIG. 14.

Referring to FIGS. 1 to 15, a first PCB 110 may be disposed in the casing body 10. The first PCB 110 may be disposed substantially horizontally (or parallel to the bottom 11) above the bottom 11. A processor 115 may be mounted on the bottom surface of the first PCB 110.

The processor 115 may process the values detected by a CO2 sensor 40, a volatile organic compound (VOC) sensor 50, a dust sensor 60, and/or a temperature/humidity sensor 70, and may transmit the processed values through a wireless communication interface 80. This data may be transmitted to a user's terminal through a communication network.

The first PCB 110 may be spaced apart from the bottom 11 of the casing body 10. At least one support rib 11b, which protrudes upwards from the bottom 11, is in contact with the bottom surface of the first PCB 110. Thereby, the position of the first PCB 110 may be maintained at a predetermined height apart from the bottom 11.

A support post 11a may protrude from the bottom 11. The support post 11a may have a cylindrical shape, and may be formed such that a screw is fastened thereinto through an open upper end thereof. The first PCB 110 may be supported by the support post 11a, and may have a screw hole formed therein to communicate with the hollow portion in the support post 11a. A screw 91 may pass through the screw hole from above and may be fastened into the hollow portion.

The height to which the support rib 11b and/or the support post 11a protrude from the bottom 11 may be set to a value that allows the processor 115 to be spaced apart from the bottom 11. Preferably, the height may be set to a value that allows the temperature/humidity sensor 70 mounted on the bottom surface of the first PCB 110 to be spaced apart from the bottom 11, which will be described later. Thus, when a first height to which the temperature/humidity sensor 70 protrudes from the bottom surface of the first PCB 110 (or the distance from the bottom surface of the first PCB 110 to the lower end of the temperature/humidity sensor 70) is greater than a second height to which the processor 115 protrudes from the bottom surface of the first PCB 110 (or the distance from the bottom surface of the first PCB 110 to the lower end of the processor 115), any one of the support rib 11b and the support post 11a needs to protrude further upwards from the bottom 11 than the first height.

Various types of sensors for detecting the quality of air may be accommodated in the casing body 10. Among the sensors accommodated in the casing body 10, the VOC sensor 50 is used to detect volatile organic compounds contained in the air. The VOC sensor 50 may include a heater embedded in a ceramic tube. The heater may be configured to use heat generated by a platinum heating wire through which current flows. The resistance of the circuit is increased and the current is decreased by the combustion reaction of the air around the heater. When gas composed of volatile organic compounds, such as formaldehyde, toluene, benzene, xylene, and an organic solvent, is contained in the air, the resistance of the circuit is decreased, and thus current flows smoothly. Therefore, the processor 115 may detect volatile organic compounds contained in the air based on the output (current or voltage) from the VOC sensor 50.

The VOC sensor 50 may be mounted on the top surface of the first PCB, particularly, in a second region that is closer to the side wall 12 than a first region occupied by the CO2 sensor 40. That is, when viewed from above, the VOC sensor 50 is disposed closer to the side wall 12 than the CO2 sensor 40. The space between the CO2 sensor 40 and the side wall 12 is utilized for the placement of the VOC sensor 50. In particular, since the VOC sensor 50 is smaller than the CO2 sensor 40, the VOC sensor 50 is mounted on the first PCB 110 without using a separate PCB. The VOC sensor 50 is disposed in the second region, which does not interfere with the first region occupied by the CO2 sensor 40, which is connected to the first PCB 110 via a header pin 150, thereby improving space utilization. The VOC sensor 50 may reach a position higher than the height at which a second PCB 120 to be described later is located.

The CO2 sensor 40 for detecting carbon dioxide (CO2) contained in the air may be accommodated in the casing body 10. The CO2 sensor 40 may be an infrared gas sensor (or a nondispersive infrared (NDIR) sensor). The NDIR sensing method is a method of calculating the concentration of a specific ingredient on the basis of the principle that gaseous substances such as CO or CO2 have a specific absorption spectrum with respect to infrared light. The CO2 sensor 40 using the NDIR sensing method may include a light emitter (not shown) for emitting infrared light of a specific frequency band that is absorbed by carbon dioxide, and a light receiver (not shown) for receiving infrared light that is not absorbed by carbon dioxide molecules.

The second PCB 120 is disposed horizontally in a predetermined first region above the first PCB 110. The CO2 sensor 40 is mounted on the second PCB 120. The header pin 150 may be provided to electrically connect the first PCB 110 to the second PCB 120. The second PCB 120 may be spaced apart from the first PCB 110 by the header pin 150.

The header pin 150 may include a pin holder 151 located on the bottom surface of the first PCB 110 and a plurality of pin terminals 152 penetrating the pin holder 151 in a vertical direction. Upper portions 152a of the pin terminals 152, which extend above the pin holder 151, may penetrate the second PCB 120 and may be soldered to the top surface of the second PCB 120, and lower portions 152b of the pin terminals 152, which extend below the pin holder 151, may penetrate the first PCB 110 and may be soldered to the bottom surface of the first PCB 110.

The CO2 sensor 40 is preferably disposed on the bottom surface of the second PCB 120. The CO2 sensor 40 is disposed such that the light emitter and the light receiver are oriented downwards. The length of the lower portion 152b of each of the pin terminals 152 needs to be set to a value that allows at least the CO2 sensor 40 to be spaced apart from the first PCB 110. The CO2 sensor 40 may detect the quality of air present within the interval between the CO2 sensor 40 and the first PCB 110. Preferably, the CO2 sensor 40 is spaced 2.8 mm or more apart from the first PCB 110.

The wireless communication interface 80 may be accommodated in the casing body 10. The wireless communication interface 80 is wirelessly connected to a communication network to transmit and receive data signals. The wireless communication interface 80 may communicate with a gateway, an access point, and/or a hub, which constitute the communication network, according to a preset communication protocol. The communication may be performed based on wireless communication technology such as Wi-Fi, ZigBee, Z-wave, or Bluetooth.

Wi-Fi was originally the brand name of Wi-Fi Alliance, but now it is commonly used to refer to wireless communication technology. Wi-Fi refers to a series of technologies that support WLAN connection between devices, WLAN connection between device connections (Wi-Fi P2P), and PAN/LAN/WAN configuration according to standards defined in IEEE 802.11. Hereinafter, the term "Wi-Fi module" indicates a wireless communication interface 80 that performs wireless communication based on Wi-Fi technology.

ZigBee is wireless network technology for performing communication by configuring a private communication network using a small-sized low-power digital radio. ZigBee is communication technology defined in IEEE 802.15. ZigBee devices are small and inexpensive and consume a relatively small amount of power, and thus are drawing attention as a solution for establishing the ubiquitous Internet, such as a home network, and are used in short-range communication for home and building networks and in industrial facility automation, logistics, human interfaces, telematics, environment monitoring, military, etc.

The ZigBee protocol is composed of a physical layer, a media access control (MAC) layer, a network layer, and an application layer. The physical layer and the MAC layer of ZigBee are defined in the IEEE 802.15.4 standard.

The ZigBee network layer supports routing and addressing for a tree structure and a mesh structure, and ZigBee Home Automation Public Profile and ZigBee Smart Energy Profile are typically used as an application profile. In addition, the new ZigBee specification RF4CE defines a simple network stack for solution of home appliance remote control and start topology. RF4CE uses a 2.4 GHz frequency band and provides encryption using AES-128.

ZigBee is generally used in fields in which a long battery life and encryption are required despite a low transmission speed, and is appropriate for periodic or intermittent data transmission or for data transmission for simple signal transmission of a sensor and an input device. ZigBee is applied to a wireless lighting switch, a home electronic power system, a traffic management system, and any other private or industrial device that requires short-range low-speed communication. ZigBee is more simple and inexpensive than other WPAN technologies such as Bluetooth or Wi-Fi. Hereinafter, the term "ZigBee module" indicates a wireless communication interface 80 that performs wireless communication based on ZigBee technology.

Z-wave is wireless transmission technology designed for a device that requires low power and a low bandwidth, such as home automation and sensor networks. Z-wave primarily aims to provide reliable communication between one or more nodes and a controller on a wireless network. Z-wave is composed of a physical layer, a MAC layer, a transmission layer, a routing layer, and an application layer. Z-wave uses a frequency band around 900 MHz (e.g. 869 MHz in Europe and 908 MHz in the United States) and a frequency band around 2.4 GHz, and provides speeds of 9.6 kbps, 40 kbps and 200 kbps. Hereinafter, the term "Z-wave module" indicates a wireless communication interface 80 that performs wireless communication based on Z-wave technology.

The third PCB 130 is disposed horizontally at a position spaced further upwards apart from the bottom 11 of the casing body 10 than the first PCB 110. The wireless communication interface 80 is mounted on the third PCB 130. The wireless communication interface 80 is preferably mounted on the bottom surface of the third PCB 130. However, in some embodiments, the wireless communication interface 80 may be mounted on the top surface of the third PCB 130.

When the bottom 11 is viewed from above, at least a portion of the third PCB 130 is disposed in a third region that does not overlap the first PCB 110. That is, when the bottom 11 is viewed from above, the first PCB 110 and the third PCB 130 may be disposed in respective regions into which the bottom 11 is substantially bisected, but may partially overlap each other.

In particular, a support rib 11c and a mount boss 11d may protrude from the bottom 11 below the third PCB 130. The support rib 11c may protrude up to a height at which the support rib 11c contacts the bottom surface of the third PCB 130 and/or the wireless communication interface 80. In addition, a retaining rib 11e may protrude from the bottom 11 so as to surround the circumference of the third PCB 130. The third PCB 130 may have a first side (e.g. a horizontal side) and a second side (e.g. a vertical side) that intersects the first side. The third PCB 130 may have a substantially rectangular shape. The retaining rib 11*e* may be formed in an "L" shape that surrounds the first side and the second side to restrain horizontal movement (shaking) of the third PCB 130.

The dust sensor 60 for detecting dust contained in the air may be accommodated in the casing body 10. The dust sensor 60 may include a heater (e.g. a circuit resistance), a light emitter (e.g. an infrared LED), a light receiver (e.g. a photodiode detector) for detecting light emitted from the light emitter, and a chamber 61, which accommodates the above components and has an air suction hole 61*h*1 and air discharge holes 61*h*2 and 61*h*3 formed therein.

Dust introduced into the chamber through the air suction hole moves upwards along with an ascending air current generated by the heater. The light (e.g. infrared light) emitted from the light emitter is scattered by the dust. The light receiver detects the scattered light and outputs a pulse waveform corresponding thereto. A portion of the chamber that surrounds the photodiode detector may be surrounded by an electromagnetic shielding member (e.g. a metal plate). The processor 115 may detect dust in the air based on the output (e.g. a pulse waveform) from the light receiver.

The fourth PCB 140 may be horizontally disposed above the second PCB 120 and the third PCB 130 inside the casing body 10. The dust sensor 60 is mounted on the top surface of the fourth PCB 140. When the bottom 11 is viewed from above, at least a portion of the third PCB 130 may overlap the fourth PCB 140.

In addition, when the bottom 11 is viewed from above, the fourth PCB 140 may overlap the CO2 sensor 40 and the VOC sensor 50. The dust sensor 60 is larger than the CO2 sensor 40, and therefore, the fourth PCB 140, on which the dust sensor 60 is mounted, is also larger than the second PCB 120, on which the CO2 sensor 40 is mounted. Thus, in the case in which the fourth PCB 140 is disposed in the same layer as the second PCB 120, the horizontal area of the air-quality detection apparatus increases. For this reason, the fourth PCB 140 is disposed above the second PCB 120 and the third PCB 130. In this case, when viewed from above, the fourth PCB 140 may completely cover the second PCB 120, and may also cover the VOC sensor 50.

The chamber 61 of the dust sensor 60 is located above the fourth PCB 140. Thus, the light emitter and the light receiver, which are accommodated in the chamber 61, as well as the air suction hole 61*h*1 and the air discharge holes 61*h*2 and 61*h*3, which are formed in the chamber 61, are located above the fourth PCB 140.

As described above, the CO2 sensor 40 is mounted on the second PCB 120 located below the fourth PCB 140. In particular, the CO2 sensor 40 is mounted on the bottom surface of the second PCB 120, which is oriented opposite the position at which the fourth PCB 140 is located. Thus, the light emitter/light receiver of the CO2 sensor 40 and the light emitter/light receiver of the dust sensor 60 may have little influence on each other. As a result, it is possible to secure the accuracy of these sensors.

A mount boss 11*f* may protrude from the bottom 11 of the casing 1. The first PCB 110 may have a first through-hole formed therein to allow the mount boss 11*f* to pass therethrough. The fourth PCB 140 may have a second through-hole formed at a position that corresponds to the position of the first through-hole. A screw 92 may pass through the second through-hole from above, and may be fastened into the mount boss 11*f*.

The fourth PCB 140 may have a first side (e.g. a horizontal side) and a second side (e.g. a vertical side) that intersects the first side. The fourth PCB 140 may have a substantially rectangular shape. A retaining rib 11*g* may protrude from the bottom 11. The retaining rib 11*g* may be formed in an "L" shape that surrounds the first side and the second side to restrain horizontal movement (shaking) of the third PCB 130.

The temperature/humidity sensor 70 is mounted on the bottom surface of the first PCB 110. Since the dust sensor 140, the CO2 sensor 40, the VOC sensor 50, and/or the wireless communication interface 80, which are heat-generating elements, are disposed above the first PCB 110, when the temperature/humidity sensor 70 is disposed under the first PCB 110, the heat generated by the above heat-generating elements is blocked and reflected by the first PCB 110, and does not reach the temperature/humidity sensor 70 hidden under the first PCB 110. Therefore, the influence of the heat generated by the heat-generating elements on the accuracy of the temperature/humidity sensor 70 is minimized.

Furthermore, when the first PCB 110 is viewed from above, the temperature/humidity sensor 70 may be disposed in a region that does not overlap the CO2 sensor 40. Since the heat generated by the CO2 sensor 40 is not perpendicularly transferred to the first PCB 110, it is possible to reduce an increase in the temperature of the first PCB 110. As a result, the amount of heat transferred to the temperature/humidity sensor 70 from the first PCB 110 through heat conduction may be reduced.

According to the air-quality detection apparatus according to the embodiment of the present disclosure, the temperature/humidity sensor 70 is provided in the casing body 10. Since the temperature/humidity sensor 70 detects the temperature and/or the humidity of air in the casing body 10, the detected value is not completely the same as that of air outside the casing body 10 (e.g. indoor air, hereinafter referred to as "external air"). However, when external air smoothly flows into and out of the casing body 10, the detection value of the temperature/humidity sensor 70 may substantially accurately indicate the state of external air.

In this respect, an air flow passage hole may be formed in the casing in order to allow external air to flow into and out of the space in which the temperature/humidity sensor 70 is accommodated. This air flow passage hole may be used only for ventilation. However, if too many holes are formed in the casing 1, they may mar the aesthetic appearance of the casing 1. Therefore, it is preferable that the air flow passage hole be formed so as to perform not only a ventilation function but also other necessary functions in order to reduce the number of holes.

The air flow passage hole may include at least one vent hole 31, 32 and 33 formed in the cover 30. The dust sensor 60 may include a chamber 61, which is mounted on the top surface of the fourth PCB 140 and into which air is introduced, and a light emitter (not shown) for emitting light into the chamber 61. The chamber 61 may have at least one communication hole 61*h*1, 61*h*2 and 61*h*3 formed therein to allow external air to flow into and out of the chamber 61.

Air introduced through the at least one vent hole 31, 32 and 33 formed in the cover 30 may be guided to the temperature/humidity sensor 70. A gap g may be formed between the first PCB 110 and the side wall 12. The space between the bottom 11 and the bottom surface of the first PCB 110, which is spaced apart from the bottom 11 by the support rib 11*b*, may communicate with the space above the first PCB 110 through the aforementioned gap.

The at least one vent hole 31, 32 and 33 includes a portion that does not overlap the at least one communication hole 61*h*1, 61*h*2 and 61*h*3. That is, the at least one vent hole 31, 32 and 33 partially communicates with the at least one communication hole 61*h*1, 61*h*2 and 61*h*3 (or overlaps the same when viewed from above). Thus, a portion of external air introduced through the at least one vent hole 31, 32 and 33 enters the chamber 61. However, since there is also a region that does not overlap the at least one vent hole 31, 32 and 33, external air introduced through the non-overlapping region flows from the casing body 10 to the outside of the chamber 61, and reaches the temperature/humidity sensor 70 via the aforementioned gap.

The at least one vent hole 31, 32 and 33 formed in the cover 30 to guide external air to the dust sensor 60 serves as the air flow passage hole through which external air to be guided to the temperature/humidity sensor 70 is introduced.

The air flow passage hole may be a gap formed between the locking hook 23 formed at the exterior panel 20 and hook passages 33*h*1 and 33*h*2 formed in the cover 30. As described above, the locking hook 23 formed at the exterior panel 20 passes through the hook passages 33*h*1 and 33*h*2 formed in the cover 30 and is fitted into the locking recess 15 formed in the casing body 10. In the process of fitting the locking hook 23 into the locking recess 15, a portion of the locking hook 23 that is connected to the lid 21 needs to be elastically deformed. Thus, if the locking hook 23 tightly passes through the hook passages 33*h*1 and 33*h*2, it is difficult to smoothly realize the coupling between the locking hook 23 and the locking recess 15. Therefore, it is preferable that a predetermined gap be present between the locking hook 23 and the hook passages 33*h*1 and 33*h*2. This gap communicates with the interior of the casing body 10.

Air introduced through the gap between the locking hook 23 and the hook passages 33*h*1 and 33*h*2 enters the casing body 10 and reaches the temperature/humidity sensor 70 through the gap between the first PCB 110 and the side wall 11.

As is apparent from the above description, the air-quality detection apparatus according to the present disclosure has the following effects.

First, since PCBs on which a CO2 sensor, a VOC sensor, and a dust sensor are mounted are disposed in a multi-layered structure in a casing body, the horizontal area of the air-quality detection apparatus may be reduced. In particular, since the CO2 sensor and a wireless communication interface are disposed substantially horizontally in the interval between the PCB on which the dust sensor is mounted and the PCB on which the VOC sensor is mounted, it is possible to realize compact arrangement of the sensors and the wireless communication interface, thereby making the air-quality detection apparatus small and compact and improving the portability thereof.

Second, when a CO2 sensor and a dust sensor, which are of an optical type, are used, since the CO2 sensor and the dust sensor are disposed at opposite positions, with a PCB interposed therebetween, the PCB may function to block light emitted from the two sensors, thereby minimizing the influence of light emitted from either one of the two sensors on the accuracy of detection by the other sensor.

Third, since PCBs on which sensors are mounted are disposed in a multi-layered structure in a casing, it is possible to conveniently perform assembly and maintenance/repair on the PCBs merely by sequentially stacking or removing the layers.

Fourth, the air quality detected by the sensors may be transmitted over a communication network, and thus a user may conveniently verify the air quality using the user's terminal.

Therefore, the present disclosure has been made in view of the above problems, and the first object of the present disclosure is to provide an air-quality detection apparatus that is compact by optimizing the arrangement of sensors and printed circuit boards (PCBs) accommodated in a casing, particularly, by realizing compact arrangement of the sensors while securing the accuracy of the respective sensors.

The second object of the present disclosure is to provide an air-quality detection apparatus in which, when a CO2 sensor and a dust sensor, which are of an optical type, are used, the influence of light emitted from either one of the two sensors on the accuracy of detection by the other sensor may be minimized.

The third object of the present disclosure is to provide an air-quality detection apparatus in which PCBs on which sensors are mounted are disposed in a multi-layered structure in a casing, thereby enabling convenient assembly and maintenance/repair of the PCBs.

The fourth object of the present disclosure is to provide an air-quality detection apparatus having an Internet-of-Things (IoT) function capable of transmitting the detected air quality over a communication network.

The fifth object of the present disclosure is to provide an air-quality detection apparatus in which a volatile organic compound (VOC) sensor or a CO2 sensor, which has a relatively large thickness, is disposed horizontally between two PCBs, which are disposed in a vertical direction such that the PCB located at the lower position is smaller than the PCB located at the upper position, and in which a PCB on which a wireless communication interface is mounted is further mounted in a region that is formed below the PBC located at the upper position but is not occupied by the PCB located at the lower position, thereby improving space utilization.

In accordance with an aspect of the present disclosure, the above and other objects can be accomplished by the provision of an air-quality detection apparatus including a CO2 sensor, a VOC sensor, and a dust sensor, which are accommodated in a casing body. The casing body may include a bottom and a side wall extending upwards from the circumference of the bottom. A first printed circuit board (PCB) may be disposed horizontally above the bottom, and second, third and fourth PCBs may be further disposed horizontally above the first PCB.

The CO2 sensor may be mounted on the second PCB, and the second PCB may be disposed in a predetermined first region above the first PCB. The VOC sensor may be mounted in a second region on the top surface of the first PCB that is closer to the side wall than the first region. The VOC sensor may reach a position higher than the height at which the second PCB is located.

The third PCB may be disposed horizontally at a position spaced further upwards apart from the bottom than the first PCB. A wireless communication interface may be mounted on the third PCB. Preferably, the wireless communication interface may be mounted on the bottom surface of the third PCB. When the bottom is viewed from above, at least a portion of the third PCB may be disposed in a third region that does not overlap the first PCB. Preferably, the first PCB and the third PCB may be disposed in respective regions into which the bottom is substantially bisected.

The fourth PCB may be disposed horizontally above the second PCB and the third PCB, and the dust sensor may be mounted on the top surface of the fourth PCB.

The CO2 sensor may be mounted on the bottom surface of the second PCB.

The CO2 sensor may be spaced 2.8 mm or more apart from the first PCB. A header pin may be further provided to cause the CO2 sensor to be spaced apart from the first PCB.

When the bottom is viewed from above, the CO2 sensor and the VOC sensor may overlap the fourth PCB. When the bottom is viewed from above, at least a portion of the third PCB may overlap the fourth PCB.

The air-quality detection apparatus may further include a mount boss protruding from the bottom. The first PCB may include a first through-hole formed therein to allow the mount boss to pass therethrough, and the fourth PCB may include a second through-hole formed at a position corresponding to the position of the first through-hole. A screw may pass through the second through-hole from above and may be fastened to the mount boss.

The fourth PCB may have a first side and a second side intersecting the first side. A retaining rib may protrude from the bottom to surround the first side and the second side of the fourth PCB.

The air-quality detection apparatus may further include a temperature/humidity sensor mounted on the bottom surface of the first PCB.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element (s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air-quality detection apparatus, comprising:
a casing body comprising a bottom and a side wall extending upwards from a circumference of the bottom;
a first printed circuit board (PCB) disposed horizontally above the bottom;
a second PCB disposed horizontally in a first region above the first PCB;
a $CO_2$ sensor mounted on the second PCB;
a volatile organic compound (VOC) sensor mounted in a second region on a top surface of the first PCB, the second region being closer to the side wall than the first region;
a third PCB on which a wireless communication interface is mounted, the third PCB being disposed horizontally at a position spaced further upwards apart from the bottom than the first PCB, at least a portion of the third PCB being disposed in a third region that does not overlap the first PCB when the bottom is viewed from above;
a fourth PCB disposed horizontally above the second PCB and the third PCB; and
a dust sensor mounted on a top surface of the fourth PCB.

2. The air-quality detection apparatus according to claim 1, wherein the $CO_2$ sensor is mounted on a bottom surface of the second PCB.

3. The air-quality detection apparatus according to claim 2, wherein the $CO_2$ sensor is spaced 2.8 mm or more apart from the first PCB.

4. The air-quality detection apparatus according to claim 1, wherein, when the bottom is viewed from above, the fourth PCB overlaps the $CO_2$ sensor and the VOC sensor.

5. The air-quality detection apparatus according to claim 1, wherein, when the bottom is viewed from above, at least a portion of the third PCB overlaps the fourth PCB.

6. The air-quality detection apparatus according to claim 1, wherein at least a portion of the $CO_2$ sensor is disposed in an interval corresponding to a difference in height between the third PCB and the first PCB.

7. The air-quality detection apparatus according to claim 6, wherein the $CO_2$ sensor comprises a portion occupying a region above the third PCB.

8. The air-quality detection apparatus according to claim 1, wherein the wireless communication interface is mounted on a bottom surface of the third PCB.

9. The air-quality detection apparatus according to claim 1, further comprising:
a mount boss protruding from the bottom,
wherein the first PCB comprises a first through-hole formed therein to allow the mount boss to pass therethrough,
wherein the fourth PCB comprises a second through-hole formed at a position corresponding to a position of the first through-hole, and
wherein the air-quality detection apparatus further comprises a screw configured to pass through the second through-hole from above and to be fastened to the mount boss.

10. The air-quality detection apparatus according to claim 9, wherein the fourth PCB comprises a first side and a second side intersecting the first side, and
wherein the air-quality detection apparatus further comprises a retaining rib protruding from the bottom to surround the first side and the second side of the fourth PCB.

11. The air-quality detection apparatus according to claim 1, further comprising:
a temperature/humidity sensor mounted on a bottom surface of the first PCB.

12. The air-quality detection apparatus according to claim 1, further comprising:
a processor configured to transmit a detection value of at least one of the $CO_2$ sensor, the VOC sensor, or the dust sensor to a communication network through the wireless communication interface.

* * * * *